United States Patent
Seo et al.

(10) Patent No.: US 9,593,940 B2
(45) Date of Patent: Mar. 14, 2017

(54) OPTICAL MEASURING METHODS AND APPARATUS

(71) Applicant: Samsung Electronics Co., Ltd., Suwon-si, Gyeonggi-do (KR)

(72) Inventors: Dong-Min Seo, Hwaseong-si (KR); Jang-Ik Park, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 161 days.

(21) Appl. No.: 14/698,167

(22) Filed: Apr. 28, 2015

(65) Prior Publication Data

US 2016/0061585 A1    Mar. 3, 2016

(30) Foreign Application Priority Data

Sep. 2, 2014  (KR) .................. 10-2014-0116479

(51) Int. Cl.
  *G01J 4/00*  (2006.01)
  *G01B 11/06*  (2006.01)
  *G01N 21/21*  (2006.01)

(52) U.S. Cl.
  CPC ........ *G01B 11/065* (2013.01); *G01B 2210/56* (2013.01); *G01N 21/211* (2013.01); *G01N 2021/213* (2013.01)

(58) Field of Classification Search
  CPC ........... G01N 21/211; G01N 2021/213; G01N 21/9501; G01B 11/0625; G01B 11/0641
  See application file for complete search history.

(56) References Cited

U.S. PATENT DOCUMENTS

| | | | |
|---|---|---|---|
| 6,922,243 B2 * | 7/2005 | Lin | G01N 21/211 356/369 |
| 7,466,428 B2 | 12/2008 | Namkoong | |
| 8,675,188 B2 | 3/2014 | Liu et al. | |
| 2002/0163649 A1 | 11/2002 | Hirose et al. | |
| 2006/0082786 A1 * | 4/2006 | Kim | G01B 11/0625 356/504 |
| 2006/0114470 A1 * | 6/2006 | Takashima | G01B 11/0625 356/453 |
| 2008/0117411 A1 * | 5/2008 | Vuong | G01N 21/956 356/73 |
| 2009/0182528 A1 * | 7/2009 | De Groot | G01B 11/06 702/167 |
| 2012/0231562 A1 | 9/2012 | Takeya et al. | |
| 2013/0044318 A1 * | 2/2013 | Cho | G01N 21/211 356/369 |
| 2013/0169958 A1 | 7/2013 | Goto et al. | |
| 2013/0314692 A1 | 11/2013 | Goto et al. | |

FOREIGN PATENT DOCUMENTS

| | | |
|---|---|---|
| JP | 2002-213924 | 7/2002 |
| JP | 2004-119452 | 4/2004 |
| JP | 2004-226178 | 8/2004 |
| JP | 2007-335557 | 12/2007 |
| KR | 1998-067203 | 10/1998 |
| KR | 10-2007-0113655 A | 11/2007 |

* cited by examiner

*Primary Examiner* — Kara E Geisel
*Assistant Examiner* — Maurice Smith
(74) *Attorney, Agent, or Firm* — Myers Bigel, P.A.

(57) ABSTRACT

In an optical measuring method, a first spectrum and a second spectrum are obtained from a pattern and a thin layer formed on the pattern by a deposition process using an ellipsometer respectively. A skew spectrum is obtained between the first spectrum and the second spectrum. A fourier transform operation is performed on the skew spectrum to calculate a thickness of the thin layer on the pattern.

19 Claims, 9 Drawing Sheets ic Property Office
OPTICAL MEASURING METHODS AND APPARATUS

CLAIM FOR PRIORITY

This application claims priority under 35 U.S.C. §119 to Korean Patent Application No. 10-2014-0116479, filed on Sep. 2, 2014 in the Korean Intellectual Property Office (KIPO), the contents of which are herein incorporated by reference in their entirety.

FIELD

Example embodiments relate to an optical measuring method and an optical measuring apparatus. More particularly, example embodiments relate to an optical measuring method of measuring a thickness of a thin layer formed on a pattern, and an optical measuring apparatus for performing the same.

BACKGROUND

In semiconductor manufacturing, optical metrology is typically used for measuring and evaluating properties such as optical properties, shapes of nano patterns, and the like, of nano samples in real time in a non-destructive manner or a non-contact manner. For example, a measuring process may be performed to measure a dimension (e.g., thickness, line width, etc) of a structure formed on a wafer.

Spectroscopic ellipsometry (SE) may be used to calculate a profile of the periodic pattern formed on the wafer (optical critical dimension).

However, through these measuring methods, it may be difficult to precisely measuring a thickness of a thin layer formed on a pattern due to correlation between an underlying structure.

SUMMARY

Example embodiments provide an optical measuring method capable of precisely measure a thickness of a thin layer on an actual pattern.

Example embodiments provide an optical measuring apparatus for performing the optical measuring method.

According to example embodiments, in an optical measuring method, a first spectrum and a second spectrum are obtained from a pattern and a thin layer formed on the pattern by a deposition process using an ellipsometer respectively. A skew spectrum is obtained between the first spectrum and the second spectrum. A fourier transform operation is performed on the skew spectrum to calculate a thickness of the thin layer on the pattern.

In example embodiments, obtaining the first spectrum and the second spectrum may include obtaining an amplitude ratio (tan(Ψ)) or phase difference (Δ) spectrum of a reflected light from the pattern and the thin layer on the pattern.

In example embodiments, performing a fourier transform operation to calculate the thickness of the thin layer may include performing a fourier transform operation on the skew spectrum to obtain a fourier transform spectrum, and determining the thickness of the thin layer based on a peak position of the fourier transform spectrum.

In example embodiments, the method may further include obtaining a plurality of third spectrums by detecting a reflected light from thin layers respectively formed on the patterns, the thin layers having different thicknesses, and obtaining a plurality of skew spectrums of the third spectrums with respect to the first spectrum. In this case, the method may further include performing a fourier transform operation on a plurality of the skew spectrums respectively to obtain a reference data for thicknesses of the thin layers.

In example embodiments, the thin layer may have a thickness of about 10 nm or less.

In example embodiments, the method may further include calculating a profile of the pattern from at least one of the first and second spectrums by using a modeling technique.

In example embodiments, the pattern may include a grating structure, and the profile of the pattern may be at least one of a width, a height and a sidewall angle of the grating structure.

According to example embodiments, in an optical measuring method, a first spectrum is obtained from a pattern by detecting a reflected light from the pattern using an ellipsometer. A thin layer is formed on the pattern. A second spectrum is obtained from a thin layer formed on the pattern using an ellipsometer. A skew spectrum is obtained between the first spectrum and the second spectrum. A fourier transform operation is performed on the skew spectrum to calculate a thickness of the thin layer on the pattern.

In example embodiments, obtaining the first spectrum and the second spectrum may include obtaining an amplitude ratio (tan(Ψ)) or phase difference (Δ) spectrum of a reflected light from the pattern and the thin layer on the pattern.

In example embodiments, calculating the thickness of the thin layer may include performing a fourier transform operation on the skew spectrum to obtain a fourier transform spectrum, and comparing the fourier transform spectrum and a reference fourier transform spectrum to determine the thickness of the thin layer.

In example embodiments, the method may further include obtaining a plurality of third spectrums by detecting a reflected light from thin layers formed on the pattern, the thin layers having different thicknesses, obtaining a plurality of skew spectrums of the third spectrums with respect to the first spectrum, and performing a fourier transform operation on the skew spectrums respectively to obtain the reference fourier transform spectrum.

In example embodiments, the thin layer may have a thickness of about 10 nm or less.

In example embodiments, the method may further include calculating a profile of the pattern from at least one of the first and second spectrums by using a modeling technique.

In example embodiments, the pattern may include a grating structure, and the profile of the pattern may be at least one of a width, a height and a sidewall angle of the grating structure.

According to example embodiments, an optical measuring apparatus includes an ellipsometer and a data processor. The ellipsometer detects a reflected light from a pattern formed by a semiconductor manufacturing process to obtain a spectrum. The data processor is connected to the ellipsometer, and includes a skew spectrum calculator for obtaining a skew spectrum between the obtained spectrums, a fourier transform operator for obtaining a fourier transform spectrum from the obtained skew spectrum by a Fourier transform, and a thickness calculator for calculating a thickness of a thin layer formed on the pattern based on the fourier transform spectrum.

In example embodiments, the ellipsometer may obtain an amplitude ratio (tan(Ψ)) or phase difference (Δ) spectrum of the reflected light from the pattern.

In example embodiments, the ellipsometer may obtain a first spectrum from the pattern and a second spectrum from the thin layer on the pattern, the skew spectrum calculator may obtain the skew spectrum between the first spectrum and the second spectrum, and the thickness calculator may compare the fourier transform spectrum and a reference fourier transform spectrum to calculate the thickness of the thin layer.

In example embodiments, the data processor may further include a memory for storing reference data for thicknesses of thin layers which are calculated by performing a Fourier transform operation on a plurality of the skew spectrums.

In example embodiments, the data processor may calculate a profile of the pattern from at least one of the first and second spectrums by using a modeling technique.

According to example embodiments, spectroscopic ellipsometry (SE) may be used to measure an optical critical dimension (OCD) of an actual pattern having a grating structure on a wafer as well as a thickness of a thin layer formed on the actual pattern.

Further, a Fourier transform operation may be performed on the skew spectrum between spectrums obtained by the ellipsometer to obtain desired thickness information and remove undesired noise components, thereby measuring a thickness of the thin layer in the range of from several to several dozen angstroms. The optical measuring method may be applied to measure a thickness of the thin layer on the underlying pattern which has a complicated structure, such as a pattern of grating structure, non-repeatable pattern, etc.

BRIEF DESCRIPTION OF THE DRAWINGS

Example embodiments will be more clearly understood from the following detailed description taken in conjunction with the accompanying drawings.

FIG. 1 is a block diagram illustrating an optical measuring apparatus in accordance with example embodiments.

FIG. 2 is a flowchart illustrating a method of measuring a thickness of a thin layer on a pattern using the optical measuring apparatus in FIG. 1.

FIG. 3 is a perspective view illustrating a pattern formed by a semiconductor manufacturing process in accordance with example embodiments.

FIG. 4 is a perspective view illustrating a thin layer formed on the pattern in FIG. 3.

FIG. 5 is a graph illustrating spectrums obtained from the pattern in FIG. 3 and the thin layer on the pattern in FIG. 4 by the optical measuring apparatus in FIG. 1.

FIG. 6 is a graph illustrating skew spectrums of the spectrums in FIG. 5.

FIG. 7 is a graph illustrating fourier transform spectrums of the skew spectrums in FIG. 6.

FIGS. 8 to 13 are cross-sectional views illustrating a method of manufacturing a semiconductor device in accordance with example embodiments.

FIG. 14 is a graph illustrating a spectrum obtained from a structure having an opening in FIG. 11 by the optical measuring apparatus in FIG. 1.

FIG. 15 is a graph illustrating spectrums obtained from a thin layer on the structure in FIG. 12 by the optical measuring apparatus in FIG. 1.

FIG. 16 is a graph illustrating skew spectrums of the spectrums in FIG. 15.

FIG. 17 is a graph illustrating fourier transform spectrums of the skew spectrums in FIG. 16.

DETAILED DESCRIPTION OF EXAMPLE EMBODIMENTS

Figure 1:
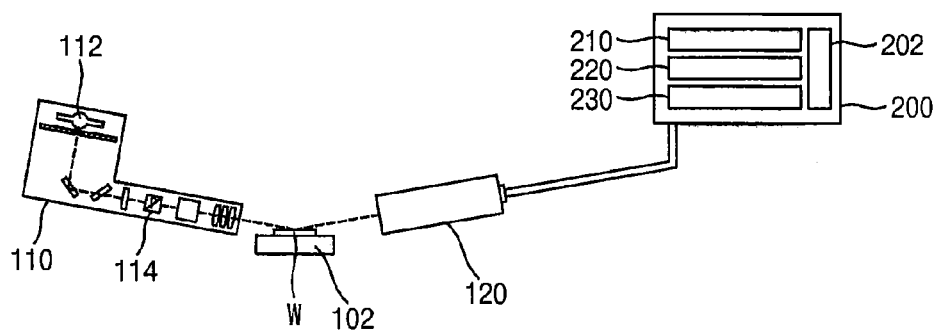
FIGS. 1 to 17 represent non-limiting, example embodiments as described herein.

Various example embodiments will be described more fully hereinafter with reference to the accompanying drawings, in which example embodiments are shown. Example embodiments may, however, be embodied in many different forms and should not be construed as limited to example embodiments set forth herein. Rather, these example embodiments are provided so that this disclosure will be thorough and complete, and will fully convey the scope of example embodiments to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, example embodiments will be explained in detail with reference to the accompanying drawings.

Figure 2:
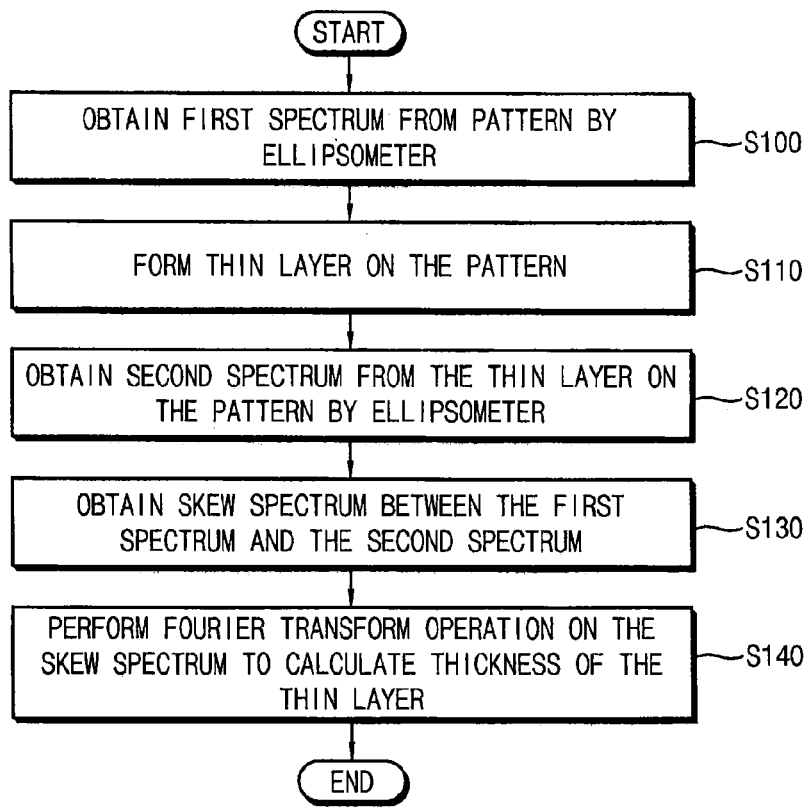
Figure 3:
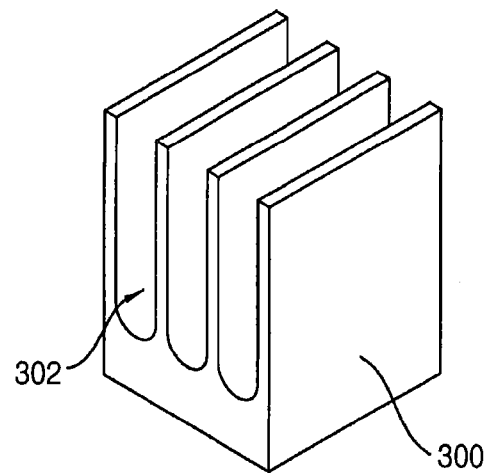
Figure 4:
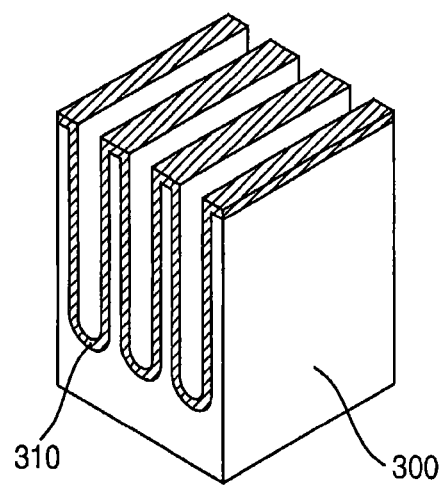
Figure 5:
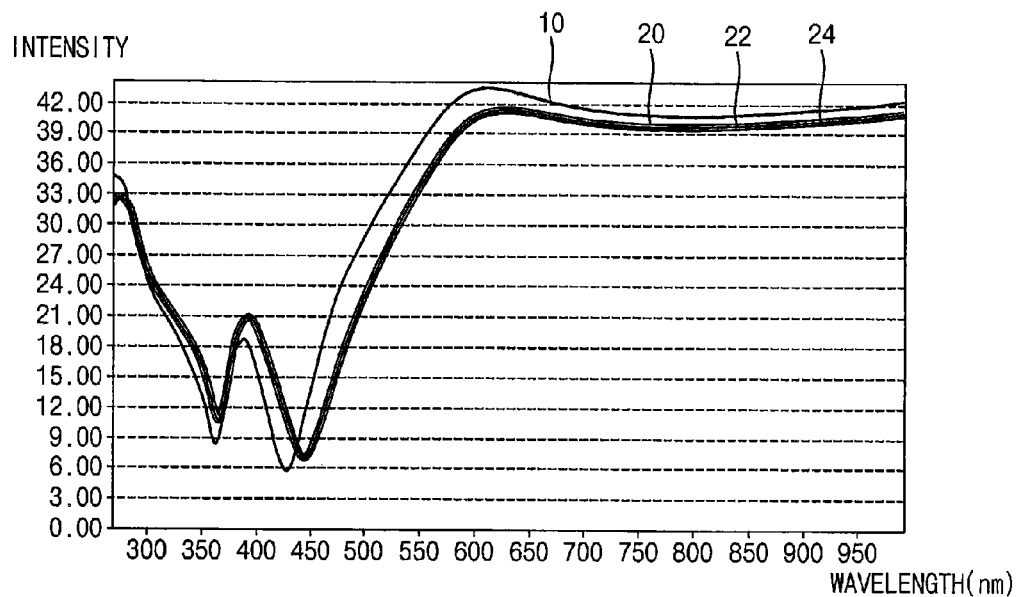
Figure 6:
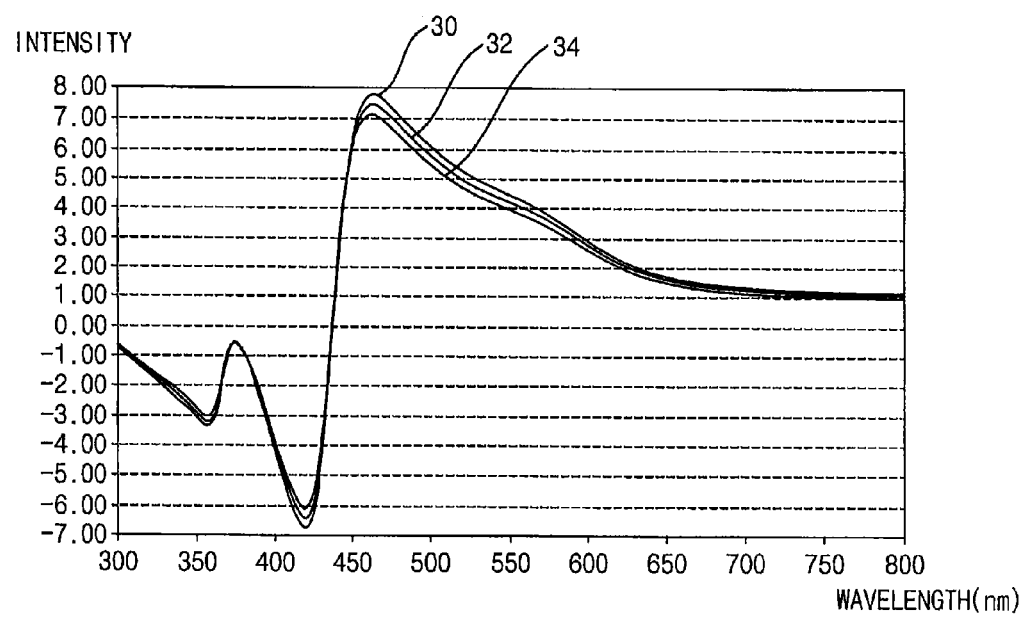
Figure 7:
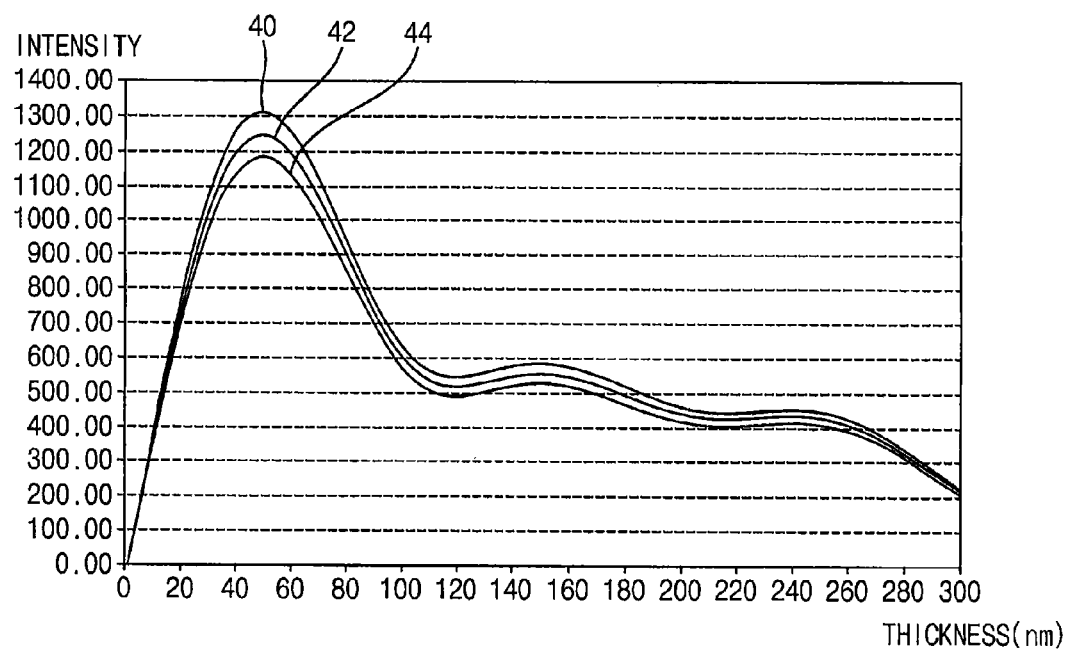

FIG. 1 is a block diagram illustrating an optical measuring apparatus in accordance with example embodiments. FIG. 2 is a flowchart illustrating a method of measuring a thickness of a thin layer on a pattern using the optical measuring apparatus in FIG. 1. FIG. 3 is a perspective view illustrating a pattern formed by a semiconductor manufacturing process in accordance with example embodiments. FIG. 4 is a perspective view illustrating a thin layer formed on the pattern in FIG. 3. FIG. 5 is a graph illustrating spectrums obtained from the pattern in FIG. 3 and the thin layer on the pattern in FIG. 4 by the optical measuring apparatus in FIG. 1. FIG. 6 is a graph illustrating skew spectrums of the spectrums in FIG. 5. FIG. 7 is a graph illustrating fourier transform spectrums of the skew spectrums in FIG. 6.

Referring to FIGS. 1 to 7, an optical measuring method according to example embodiments may be used to monitor a semiconductor process for forming semiconductor devices such as DRAM, VNAND, etc. through non-destructive testing.

An optical measuring apparatus 100 in FIG. 1 may include a measuring instrument configured to perform spectroscopic ellipsometry (SE), which may measure properties such as thickness of a thin layer and profile of a grating structure formed on a wafer. For example, the profile of the grating structure may include a width, a height, a sidewall angle, etc.

The wafer may refer to a substrate formed of a semiconductor or non-semiconductor material. The wafer may include one or more layers formed on the substrate. For example, such layers may include, but are not limited to, a resist, a dielectric material or a conductive material. Additionally, the wafer may include a plurality of dies, each having a repeatable pattern features.

As illustrated in FIG. 1, in example embodiments, the optical measuring apparatus 100 may include an ellipsometer 120. In this case, a wafer W may be supported on a stage 102, and then, light from a light irradiation portion 110 may be incident upon the wafer W. In particular, the light from a light source 112 may be polarized by a polarizer 114 to be decomposed into an s and p component, and then, the s and p components may be incident upon a structure on the wafer W.

Then, a reflected light from the wafer W may be detected using the ellipsometer 120 to obtain a spectrum. For example, the ellipsometer 120 may generate a reflection ratio spectrum of the s and p components, that is, amplitude ratio (tan(Ψ)) spectrum and/or phase difference (Δ) spectrum.

In example embodiments, a data processor 200 may be connected to the ellipsometer 120, and remove noises from the obtained spectrums and use desired signal components to calculate a thickness of a thin layer formed on a pattern.

In particular, the data processor 200 may include a skew spectrum calculator 210 for obtaining skew spectrums between the obtained spectrums, a fourier transform operator 220 for obtaining a fourier transform spectrum from the obtained skew spectrum by a Fourier transform, and a thickness calculator 230 for calculating a thickness of the thin layer formed on the pattern based on the fourier transform spectrum.

The data processor 200 may be connected to the ellipsometer 120 via data transmission media including cable transmission link and/or wireless transmission link. The data processor 200 may receive the data (spectrums) that are generated by the ellipsometer 120.

The data processor 200 may further include a memory 202 for storing spectrums which are received from the ellipsometer 120, spectrums which are generated by the fourier transform operator 220, and reference data for thicknesses of thin layers calculated based on the fourier transform spectrums.

In additions, the data processor 200 may use a modeling technique such as rigorous coupled wave analysis (RCWA), to calculate a profile (e.g., width, height, sidewall angle, etc) of a grating structure formed on the wafer from the spectrums obtained by the ellipsometer 120.

Hereinafter, a method of measuring a thickness of a thin layer formed on a pattern using the optical measuring apparatus will be explained Referring to FIGS. 2 to 5; after a semiconductor manufacturing process is performed on the wafer W to form a pattern 300, a reflected light from the pattern 300 may be detected to obtain a first spectrum 10 (S100).

For example, after a hard mask (not illustrated) is formed on a substrate, the substrate may be etched using the hard mask as an etching mask to form the pattern 300 having the trench 302. For example, the substrate may include a silicon substrate.

Then, the substrate may be loaded on the stage 120 of the optical measuring apparatus 100, and then, a reflected light from the pattern 300 may be detected using the ellipsometer 120 to obtain the first spectrum 10 in FIG. 5.

Then, after a deposition process is performed to form a thin layer 310 on the pattern 300 (S110), a reflected light from the thin layer 310 on the pattern 300 may be detected to obtain second spectrums 20, 22, 24 (S120).

For example, a deposition process such as a chemical vapor deposition process may be performed to form the thin layer 310 on the pattern 300. The thin layer 310 may have a thickness of about 10 nm or less. The thin layer may include silicon oxide.

Then, the substrate may be loaded on the stage 120 of the optical measuring apparatus 100, and then, a reflected light from the thin layer 310 on the pattern 300 may be detected using the ellipsometer 120 to obtain the second spectrums 20, 22, 24 in FIG. 5.

The first spectrum 10 in FIG. 5 represents a simulation result of the spectrum obtained from the pattern before performing the deposition process, the second spectrums 20, 22 and 24 in FIG. 5 represent simulation results of the spectrums obtained from the thin layer on the pattern after performing the deposition process, each spectrum being obtained from the thin layer having different thicknesses. In here, the second spectrum 20 may be the spectrum obtained from the thin layer having a thickness of about 19 Å, the second spectrum 22 may be the spectrum obtained from the thin layer having a thickness of about 20 Å, and the second spectrum 24 may be the spectrum obtained from the thin layer having a thickness of about 21 Å.

Referring to FIG. 6, skew spectrums 30, 32, 34 between the first spectrum 10 and the second spectrums 20, 22, 24 may be obtained (S130).

In example embodiments, the skew spectrum calculator 210 of the data processor 200 may calculate the skew spectrum as a difference spectrum between the first spectrum 10 and the second spectrums 20, 22, 24 stored in the memory 202.

In FIG. 6, the skew spectrum 30 may be the difference spectrum between the first spectrum 10 and the second spectrum 20 of the thin layer having a thickness of about 19 Å. The skew spectrum 32 may be the difference spectrum between the first spectrum 10 and the second spectrum 22 of the thin layer having a thickness of about 20 Å. The skew spectrum 34 may be the difference spectrum between the first spectrum 10 and the second spectrum 24 of the thin layer having a thickness of about 21 Å.

Referring to FIG. 7, a frequency analysis may be performed on the skew spectrums 30, 32, 34 to calculate a thickness of the thin layer 310 (S140).

In example embodiments, the fourier transform operator 220 may perform a Fourier transform operation on the skew spectrums 30, 32, 34 to obtain fourier transform spectrums 40, 42, 44 and the thickness calculator 230 may determine a thickness of the thin layer 310 based on a peak position of the fourier transform spectrums 40, 42, 44.

In FIG. 7, the fourier transform spectrum 40 may be a fast fourier transform (FFT) spectrum of the skew spectrum 30 for the thin layer having a thickness of about 19 Å. The fourier transform spectrum 42 may be a fast fourier transform (FFT) spectrum of the skew spectrum 32 for the thin layer having a thickness of about 20 Å. The fourier transform spectrum 44 may be a fast fourier transform (FFT) spectrum of the skew spectrum 34 for the thin layer having a thickness of about 21 Å.

The fourier transform spectrum obtained by the fast fourier transform operation may change sensitively to a thickness variation of the thin layer and undesired noise components may be removed from the spectrum. Accordingly, the peak of the fourier transform spectrum may be analyzed to easily calculate the thickness of the thin layer.

In example embodiments, the fourier transform spectrum and a reference fourier transform spectrum may be compared with each other to calculate the thickness of the thin layer.

The fourier transform spectrums for the thin layers having different thicknesses in FIG. 7 may be stored in the memory 202. The stored fourier transform spectrums may be a reference fourier transform spectrum for each of the thin layers having different thicknesses. The fourier transform spectrums calculated from the spectrums which are obtained from the pattern and the thin layer on the pattern may be compared with the reference fourier transform spectrums stored in the memory 202, and then, one of the reference fourier transform spectrums most similar to any fourier transform spectrum may be selected and used to calculate a thickness of the thin layer from which the fourier transform spectrum obtained.

In addition, a modeling technique such as rigorous coupled wave analysis (RCWA) may be performed on the first spectrum 10 and the second spectrums 20, 22, 24 to calculate a profile (e.g., width, height, sidewall angle, etc) of the pattern.

As mentioned above, spectroscopic ellipsometry (SE) may be used to measure an optical critical dimension (OCD) of an actual pattern having a grating structure on a wafer as well as a thickness of a thin layer formed on the actual pattern.

Additionally, a Fourier transform operation may be performed on the skew spectrum between spectrums obtained by the ellipsometer to obtain desired thickness information and remove undesired noise components, thereby measuring a thickness of the thin layer on the underlying pattern in the range of from several to several dozen angstroms. The optical measuring method may be applied to measure a thickness of the thin layer on the underlying pattern which has a complicated structure, such as a pattern of grating structure, non-repeatable pattern, etc. The optical measuring method may be applied similarly to spectrums obtained by dual beam spectrometry.

Figure 14:
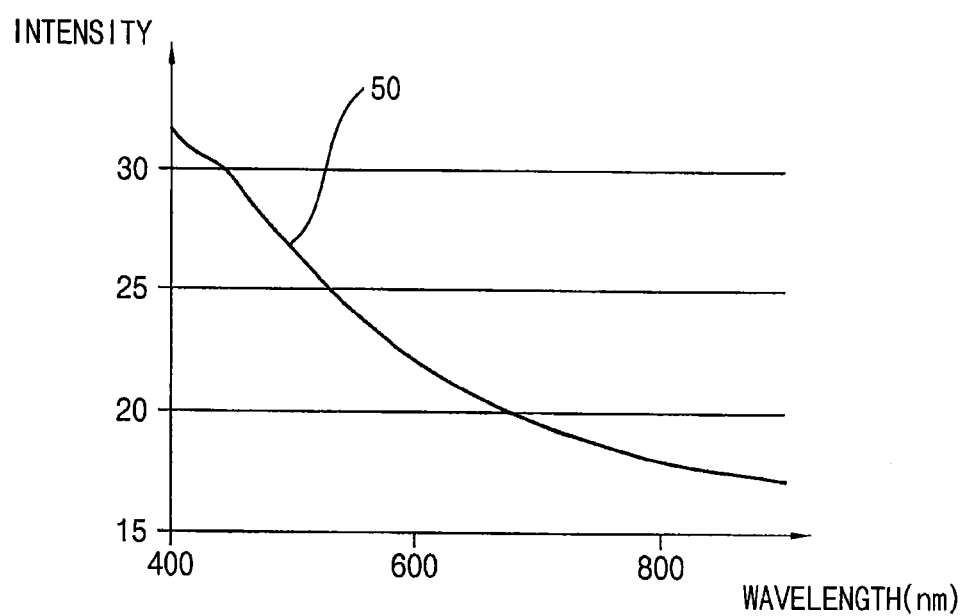
Figure 15:
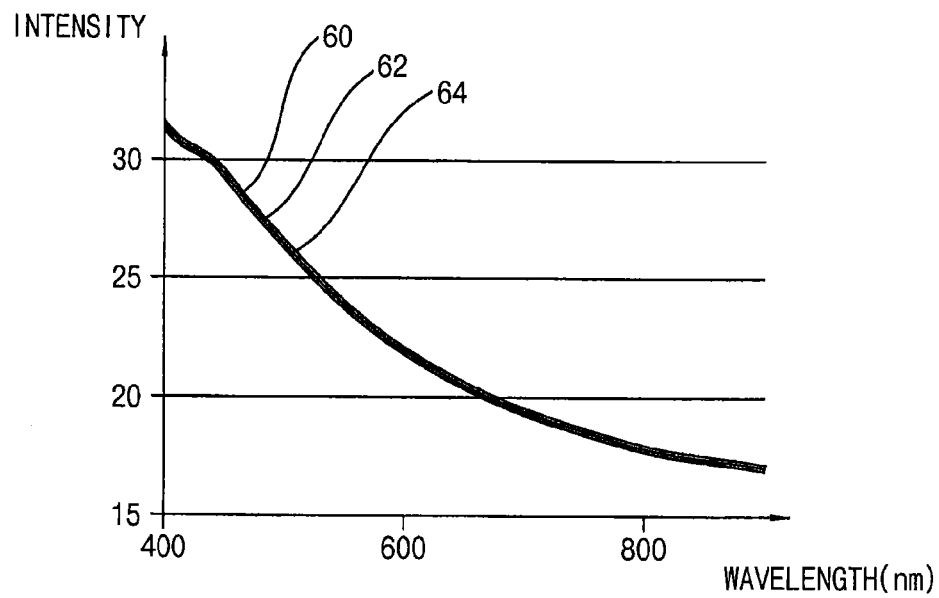
Figure 16:
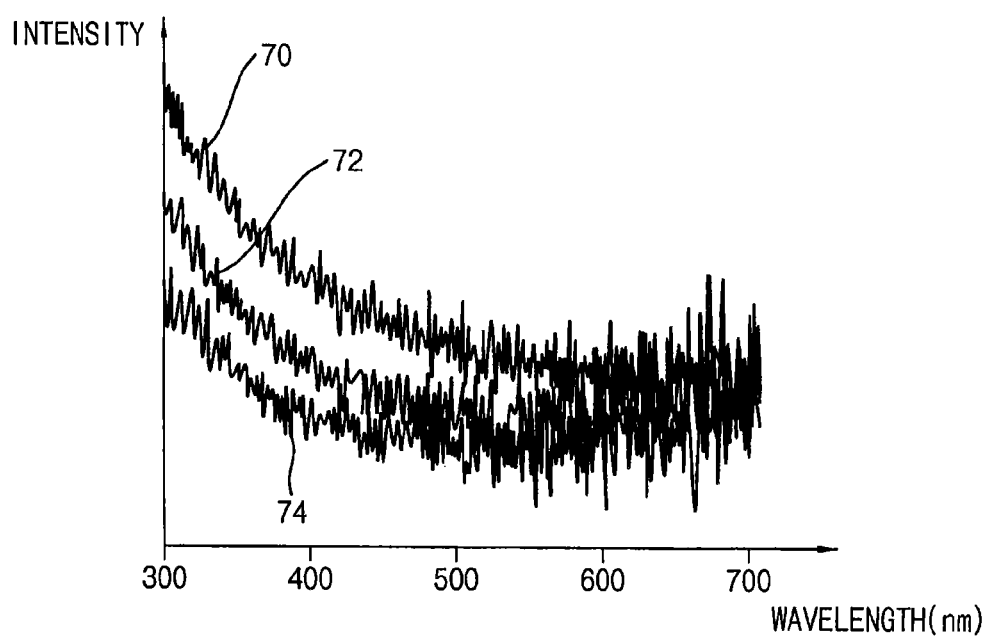
Figure 17:
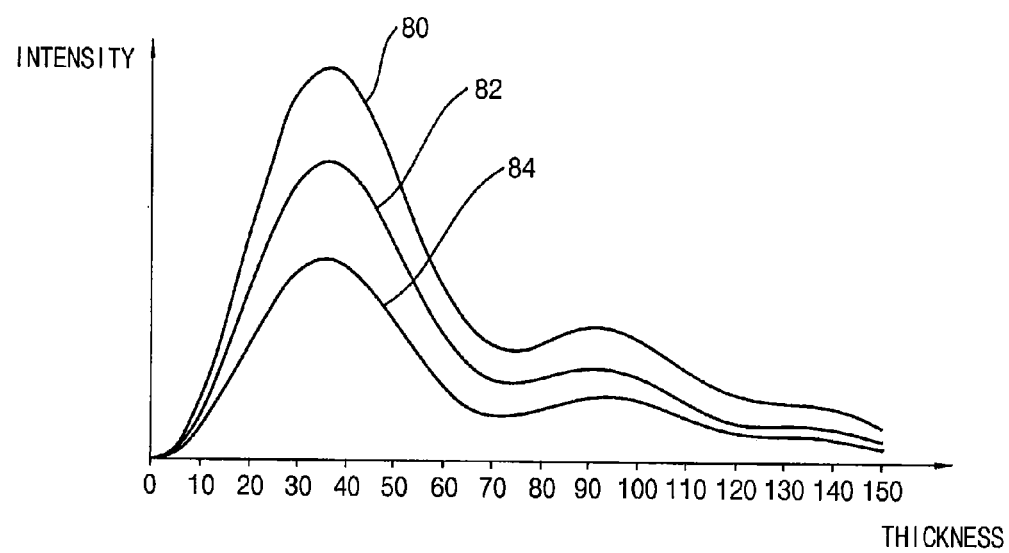

FIGS. 8 to 13 are cross-sectional views illustrating a method of manufacturing a semiconductor device in accordance with example embodiments. FIG. 14 is a graph illustrating a spectrum obtained from a structure having an opening in FIG. 11 by the optical measuring apparatus in FIG. 1. FIG. 15 is a graph illustrating spectrums obtained from a thin layer on the structure in FIG. 12 by the optical measuring apparatus in FIG. 1. FIG. 16 is a graph illustrating skew spectrums of the spectrums in FIG. 15. FIG. 17 is a graph illustrating fourier transform spectrums of the skew spectrums in FIG. 16.

Figure 8:
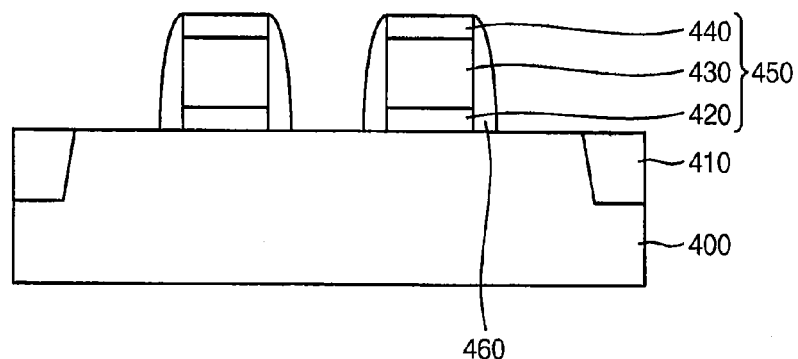

Referring to FIG. 8, an isolation layer 410 may be formed on a substrate 400, and a dummy gate structure 450 and a spacer 460 may be formed on the substrate 400 and the isolation layer 410.

The substrate 400 may be a silicon substrate, a germanium substrate, a silicon-germanium substrate, a silicon-on-insulator (SOI) substrate, a germanium-on-insulator (GOI) substrate, etc. The substrate 400 may be divided into a field region on which the isolation layer 410 is formed and an active region on which no isolation layer is formed. In example embodiments, the isolation layer 410 may be formed by a shallow trench isolation (STI) process, and may be formed to include an oxide, e.g., silicon oxide.

The dummy gate structure 450 may be formed by sequentially stacking a gate insulation layer and a dummy gate electrode layer and a gate mask layer, patterning the gate mask layer by a photolithography process using a photoresist pattern (not shown) to form a gate mask 440, and patterning the dummy gate electrode layer and the gate insulation layer using the gate mask 440 as an etching mask. Thus, the dummy gate structure 450 may be formed to include a gate insulation layer pattern 420, a dummy gate electrode 430 and a gate mask 440 sequentially stacked on the substrate 400 and the isolation layer 410.

The dummy gate structure 450 may be formed only on the active region of the substrate 400. Alternatively, the dummy gate structure 450 also may be formed on the isolation layer 410 so as to be formed on both of the active region and the field region of the substrate 400. In example embodiments, the dummy gate structure 450 may be formed to extend in a first direction on the substrate 400 and the isolation layer 410, and a plurality of dummy gate structures 450 may be formed in a second direction substantially perpendicular to the first direction.

A spacer layer covering the dummy gate structure 450 may be formed on the substrate 400 and the isolation layer 410, and etched by an anisotropic etching process to form a spacer 460 on a sidewall of the dummy gate structure 450. For example, the spacer layer may be formed to include a nitride, e.g., silicon nitride. The spacer layer may be formed by an ALD process, a CVD process, etc.

Figure 9:
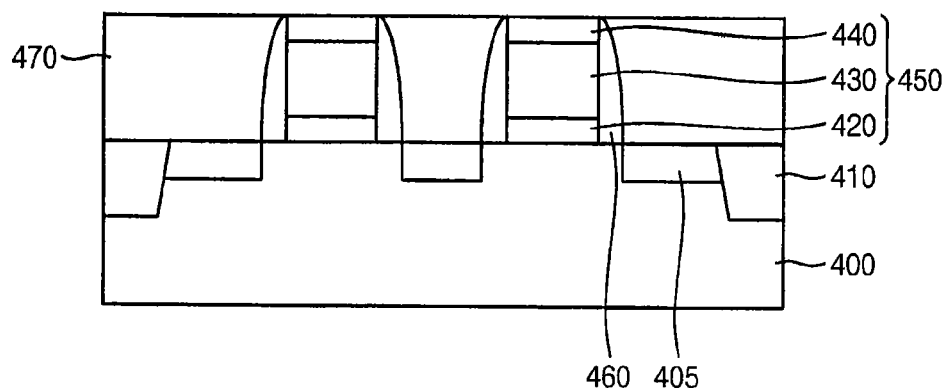
Figure 10:
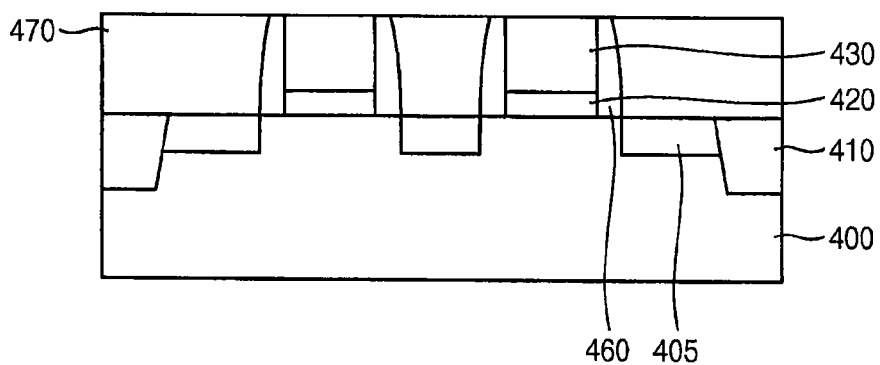

Referring to FIGS. 9 and 10, an impurity region 405 may be formed at an upper portion of the active region of the substrate 400 adjacent to the dummy gate structure 450.

Particularly, the active region of the substrate 400 may be partially removed using the dummy gate structure 450 and the spacer 460 as an etching mask to form a trench (not shown) at an upper portion of the active region, and the impurity region 405 may be formed to fill the trench.

In example embodiments, a selective epitaxial growth (SEG) process may be performed using a top surface of the substrate 400 exposed by the trench as a seed layer to form the impurity region 405. The SEG process may be performed using, e.g., dichlorosilane ($SiH_2Cl_2$) gas, germane ($GeH_4$) gas, etc., as a source gas, and thus a single crystalline silicon-germanium layer may be formed. In example embodiments, p-type impurity source gas, e.g., diborane ($B_2H_6$) gas also may be used to form a single crystalline silicon-germanium layer doped with p-type impurities. In this case, the impurity region 405 may serve as a source/drain region of a positive-channel metal oxide semiconductor (PMOS) transistor.

Alternatively, the impurity region 405 also may be formed by implanting impurities into an upper portion of the substrate 400 adjacent to the dummy gate structure 450.

Then, a first insulating interlayer 470 covering the dummy gate structure 450 and the spacer 460 may be formed on the substrate 400 and the isolation layer 410, and the first insulating interlayer 470 may be planarized until a top surface of the dummy gate electrode 430 may be exposed.

For example, the first insulating interlayer 470 may be formed to include silicon oxide. In example embodiments, the planarization process may be performed by a chemical mechanical polishing (CMP) process and/or an etch back process.

The first insulating interlayer 470 may be planarized so as to have a top surface substantially coplanar with a top surface of the dummy gate electrode 430. In example embodiments, the planarization process may be performed using the top surface of the dummy gate electrode 430 as a polishing endpoint.

Figure 11:
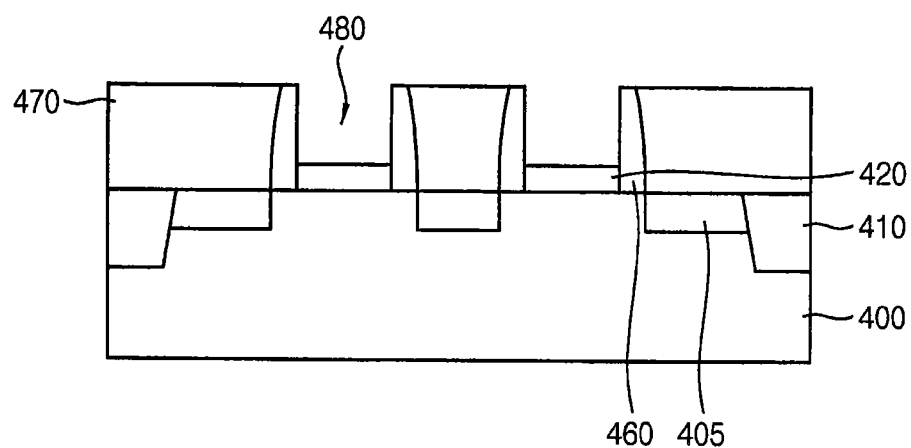
Figure 12:
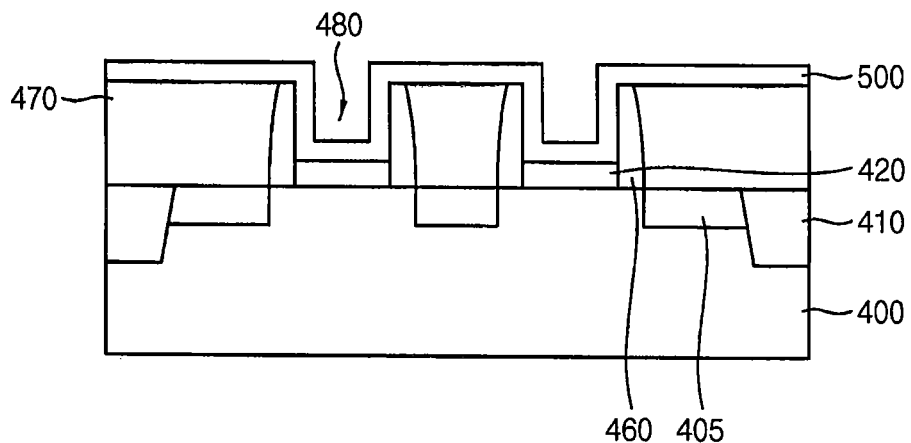

Referring to FIGS. 11 and 12, the dummy gate electrode 430 may be removed to form an opening 480 exposing a top surface of the gate insulation layer pattern 420, and then, a high-k dielectric layer 500 may be formed on the exposed top surface of the gate insulation layer pattern 420, a sidewall of the opening 480, and a top surface of the first insulating interlayer 470.

In example embodiments, the dummy gate electrode 430 may be sufficiently removed by performing a dry etch process and performing a wet etch process, to form a structure having the opening 480. That is, the opening 480 may be defined by the top surface of the gate insulation layer pattern 420 and an inner sidewall of the spacer 460. The wet etch process may be performed using HF as an etching solution.

The high-k dielectric layer 500 may be formed to include a metal oxide having a high dielectric constant, e.g., hafnium oxide, tantalum oxide, zirconium oxide, etc. The high-k dielectric layer 500 may be a thin layer having a thickness of about 10 nm or less. The high-k dielectric layer may be formed by a deposition process such as CVD process, an ALD process, etc.

Then, the optical measuring method as described with reference to FIGS. 1 to 7 may be used to measure a thickness of the high-k dielectric layer 500 formed on the structure, to thereby monitor the deposition process.

Referring to FIGS. 14 to 17, first, a reflected light from the structure having the opening 480 in FIG. 11 may be detected to obtain a first spectrum 50 in FIG. 14.

In particular, the substrate 400 may be loaded on a stage 102 of a process chamber of the measuring equipment 100. A reflected light from the structure in FIG. 11 may be detected using the ellipsometer 120 to obtain the first spectrum 50. For example, the ellipsometer 120 may generate a reflection ratio spectrum of the s and p components, that is, amplitude ratio (tan($\Psi$)) spectrum and/or phase difference ($\Delta$) spectrum. The first spectrum 50 may be stored in the memory 202 of the data processor 200.

Then, a reflected light from the high-k dielectric layer 500 on the structure may be detected to obtain second spectrums 60, 62, 64 in FIG. 15.

In particular, after the above deposition process is performed on the substrate 400 to form the high-k dielectric layer 500 on the structure, the substrate may be loaded again on the stage 102 of the optical measuring apparatus 100. A reflected light from the high-k dielectric layer 500 on the structure in FIG. 12 may be detected using the ellipsometer 120 to obtain second spectrums 60, 62, 64. For example, the ellipsometer 120 may generate a reflection ratio spectrum of the s and p components, that is, amplitude ratio (tan($\Psi$)) spectrum and/or phase difference ($\Delta$) spectrum. The second spectrums 60, 62, 64 may be stored in the memory 202 of the data processor 200.

The second spectrums 60, 62 and 64 in FIG. 15 represent simulation results of the spectrums obtained from the hafnium oxide layer formed on the pattern by the deposition process, each spectrum being obtained of the hafnium oxide layer having different thicknesses. In here, the second spectrum 60 may be the spectrum obtained from the hafnium oxide layer having a thickness of about 18 Å, the second spectrum 62 may be the spectrum obtained from the hafnium oxide layer having a thickness of about 20 Å, and the second spectrum 64 may be the spectrum obtained from the hafnium oxide layer having a thickness of about 22 Å.

As illustrated in FIG. 16, skew spectrums 70, 72, 74 between the first spectrum 50 and the second spectrums 60, 62, 64 may be obtained.

The skew spectrum calculator 210 of the data processor 200 may calculate the skew spectrum as a difference spectrum between the first spectrum 50 and the second spectrums 60, 62, 64 stored in the memory 202.

In FIG. 16, the skew spectrum 70 may be the difference spectrum between the first spectrum 50 and the second spectrum 60 of the hafnium oxide layer having a thickness of about 18 Å. The skew spectrum 72 may be the difference spectrum between the first spectrum 10 and the second spectrum 62 of the hafnium oxide layer having a thickness of about 20 Å. The skew spectrum 74 may be the difference spectrum between the first spectrum 10 and the second spectrum 64 of the hafnium oxide layer having a thickness of about 20 Å.

Then, as illustrated in FIG. 17, a frequency analysis may be performed on the skew spectrums 70, 72, 74 to calculate a thickness of the high-k dielectric layer 510.

The fourier transform operator 220 may perform a Fourier transform operation on the skew spectrums 70, 72, 74 to obtain a fourier transform spectrums 80, 82, 84 and the thickness calculator 230 may determine a thickness of the high-k dielectric layer 500 based on a peak position of the fourier transform spectrums 80, 82, 84.

In FIG. 17, the fourier transform spectrum 80 may be a fast fourier transform (FFT) spectrum of the skew spectrum 70 for the hafnium oxide layer having a thickness of about 18 Å. The fourier transform spectrum 82 may be a fast fourier transform (FFT) spectrum of the skew spectrum 72 for the hafnium oxide layer having a thickness of about 20 Å. The fourier transform spectrum 84 may be a fast fourier transform (FFT) spectrum of the skew spectrum 74 for the hafnium oxide layer having a thickness of about 22 Å.

Spectroscopic ellipsometry (SE) may be used to obtain spectrums from the structure in FIG. 11 and the high-k dielectric layer on the structure in FIG. 12, a Fourier transform operation may be performed on a skew spectrum between the spectrums to obtain a fourier transform spectrum. The fourier transform spectrum and a reference fourier transform spectrum stored in the memory 202 may be compared with each other to calculate a thickness of the high-k dielectric layer 500. The layer having a thickness ranging from several to several dozen angstroms may be measured. When the calculated thickness of the high-k dielectric layer falls within an allowable range, a following process may proceed.

As mentioned above, spectroscopic ellipsometry (SE) may be used to measure a thickness of a thin layer in the range of from several to several dozen angstroms formed on an actual pattern on a wafer.

Figure 13:
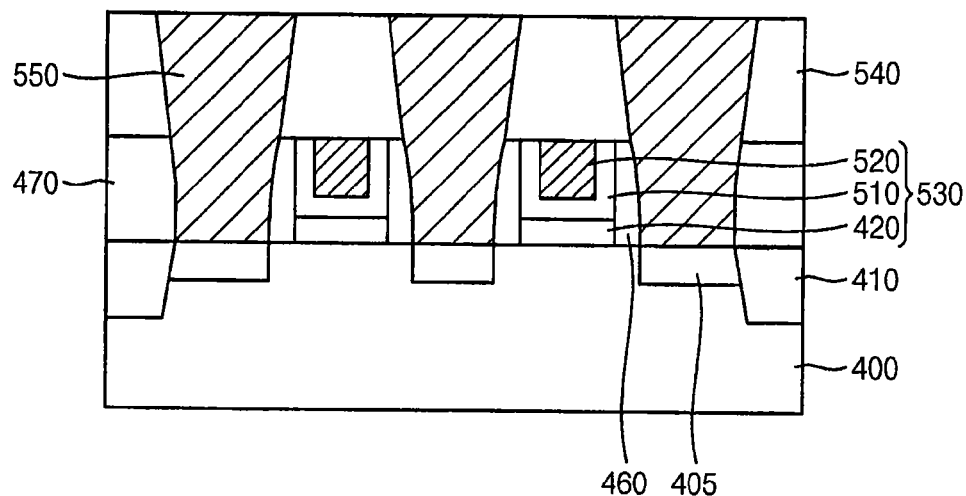

Referring to FIG. 13, a gate electrode layer (not shown) may be formed on the high-k dielectric layer 500 to sufficiently fill the opening 480, and then, a gate structure 530 including the gate insulation layer pattern 420, a high-k dielectric layer pattern 510 and a gate electrode 520 sequentially stacked may be formed on the substrate 400 and/or the isolation layer 410.

The gate electrode layer may be formed to include a material having a low resistance, e.g., a metal such as aluminum, copper, tantalum, etc., or a metal nitride thereof by an ALD process, a physical vapor deposition (PVD) process, etc. Alternatively, the gate electrode layer may be formed to include doped polysilicon.

Then, the gate electrode layer and the high-k dielectric layer 500 may be planarized until the top surface of the first insulating interlayer 470 may be exposed to form the high-k dielectric layer pattern 510 on the top surface of the gate insulation layer pattern 420 and the sidewall of the opening 480, and the gate electrode layer 520 filling a remaining portion of the opening 480 on the high-k dielectric layer pattern 510. Thus, a bottom and a sidewall of the gate electrode 520 may be covered by the high-k dielectric layer pattern 510. In example embodiments, the planarization process may be performed by a CMP process and/or an etch back process.

By the above processes, the gate structure 530 including the gate insulation layer pattern 420, the high-k dielectric layer pattern 510 and the gate electrode 520 sequentially stacked may be formed on the substrate 400 and/or the isolation layer 410.

Then, a second insulating interlayer 540 may be formed on the first insulating interlayer 470 and the gate structure 530 and the spacer 460, and a second opening may be formed through the first and second insulating interlayers 470 and 550 to expose a top surface of the impurity region 405. Then, a contact plug 550 may be formed to fill the second opening.

The second insulating interlayer 540 may be formed to include an oxide, e.g., silicon oxide. The second insulating interlayer 540 may be formed to include a material substantially the same as or different from that of the first insulating interlayer 470.

The second opening may be formed by forming a photoresist pattern (not shown) and performing a dry etch process using the photoresist pattern as an etching mask.

The contact plug 550 may be formed by forming a barrier layer (not shown) on the top surface of the impurity region 405, the sidewall of the second opening and the top surface of the second insulating interlayer 550, forming a conductive layer on the barrier layer to sufficiently fill a remaining portion of the second opening, and planarizing the conductive layer and the barrier layer until the top surface of the second insulating interlayer 550 may be exposed. In example embodiments, the barrier layer may be formed to include a metal or a metal nitride, and the conductive layer may be formed to include doped polysilicon, a metal, a metal nitride and/or a metal silicide.

By the above processes, the semiconductor device may be manufactured.

The above semiconductor device may be applied to various types of memory devices including gate structures. For example, the semiconductor device may be applied to gate structures of logic devices such as central processing units (CPUs), main processing units (MPUs), or application processors (APs), etc. Additionally, the semiconductor device may be applied to gate structures in a memory cell region or a peripheral circuit region of volatile memory devices such as DRAM devices or SRAM devices, or non-volatile memory devices such as flash memory devices, PRAM devices, MRAM devices, RRAM devices, etc.

Semiconductor devices such as DRAM, VNAND, etc. manufactured using the optical measuring method and optical measuring system may be used to various systems such as a computing system. The system may be applied to computers, portable computers, laptop computers, PDAs, tablets, mobile phones, digital music players, etc.

The foregoing is illustrative of example embodiments and is not to be construed as limiting thereof. Although a few example embodiments have been described, those skilled in the art will readily appreciate that many modifications are possible in example embodiments without materially departing from the novel teachings and advantages of the present invention. Accordingly, all such modifications are intended to be included within the scope of example embodiments as defined in the claims. In the claims, means-plus-function clauses are intended to cover the structures described herein as performing the recited function and not only structural equivalents but also equivalent structures. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. An optical measuring method, comprising:
   obtaining, via an ellipsometer, a first spectrum from a pattern and a second spectrum from a thin layer formed on the pattern by a deposition process;
   obtaining a skew spectrum between the first spectrum and the second spectrum; and
   performing a fourier transform operation on the skew spectrum to calculate a thickness of the thin layer on the pattern.

2. The method of claim 1, wherein obtaining the first spectrum and the second spectrum comprises obtaining an amplitude ratio (tan(Ψ)) or phase difference (Δ) spectrum of a reflected light from the pattern and the thin layer on the pattern.

3. The method of claim 1, wherein performing a fourier transform operation to calculate the thickness of the thin layer comprises:
performing a fourier transform operation on the skew spectrum to obtain a fourier transform spectrum; and
determining the thickness of the thin layer based on a peak position of the fourier transform spectrum.

4. The method of claim 1, further comprising:
obtaining a plurality of third spectrums by detecting a reflected light from thin layers respectively formed on a plurality of patterns, the thin layers having different thicknesses; and
obtaining a plurality of skew spectrums of the third spectrums with respect to the first spectrum.

5. The method of claim 4, further comprising:
performing a plurality of fourier transform operations on the plurality of the skew spectrums respectively to obtain reference data for the thicknesses of the thin layers.

6. The method of claim 1, wherein the thin layer has a thickness of about 10 nm or less.

7. The method of claim 1, further comprising:
calculating a profile of the pattern from at least one of the first and second spectrums by using a modeling technique.

8. The method of claim 7, wherein the pattern comprises a grating structure, and the profile of the pattern is at least one of a width, a height and a sidewall angle of the grating structure.

9. An optical measuring method, comprising:
obtaining a first spectrum from a pattern by detecting a reflected light from the pattern using an ellipsometer;
forming a thin layer on the pattern;
obtaining a second spectrum from the thin layer formed on the pattern using the ellipsometer;
obtaining a skew spectrum between the first spectrum and the second spectrum; and
performing a fourier transform operation on the skew spectrum to calculate a thickness of the thin layer on the pattern.

10. The method of claim 9, wherein obtaining the first spectrum and the second spectrum comprises obtaining an amplitude ratio (tan(Ψ)) or phase difference (Δ) spectrum of the reflected light from the pattern and the thin layer on the pattern.

11. The method of claim 9, wherein calculating the thickness of the thin layer comprises:
performing a fourier transform operation on the skew spectrum to obtain a fourier transform spectrum; and
comparing the fourier transform spectrum and a reference fourier transform spectrum to determine the thickness of the thin layer.

12. The method of claim 11, further comprising:
obtaining a plurality of third spectrums by detecting a reflected light from thin layers formed on the pattern, the thin layers having different thicknesses;
obtaining a plurality of skew spectrums of the third spectrums with respect to the first spectrum; and
performing a plurality of fourier transform operations on the skew spectrums respectively to obtain the reference fourier transform spectrum.

13. The method of claim 9, wherein the thickness of the thin layer is about 10 nm or less.

14. The method of claim 9, further comprising:
calculating a profile of the pattern from at least one of the first and second spectrums by using a modeling technique.

15. The method of claim 14, wherein the pattern comprises a grating structure, and the profile of the pattern is at least one of a width, a height and a sidewall angle of the grating structure.

16. An optical measuring apparatus, comprising:
a stage configured to support a wafer having a pattern and a thin layer disposed on the pattern;
a light source configured to irradiate the wafer;
an ellipsometer configured to detect a first spectrum relflected from the pattern and a second spectrum reflected from the thin layer;
a data processor connected to the elliposmeter, wherein the data processor comprises a skew spectrum calculator configured to obtain skew spectrums between the reflection spectrums generated by the ellipsometer;
a fourier transform operator configured to obtain fourier transform spectrums from the skew spectrums; and
a thickness calculator configured to calcualte a thickness of the thin layer.

17. The optical measuring apparatus of claim 16, further comprising a polarizer that is configured to decompose light from the light source into s and p components that are incident on the wafer, and wherein the ellipsometer is configured to generate a reflection ratio spectrum of the s and p components.

18. The optical measuring apparatus of claim 16, further comprising a data processor connected to the ellipsometer, wherein the data processor is configured to remove noise from the reflection spectrums generated by the ellipsometer.

19. The optical measuring apparatus of claim 16, wherein the data processor is configured to utilize a rigorous coupled wave analysis (RCWA) modeling technique to calculate a profile of a structure formed on the wafer using the reflection spectrums generated by the ellipsometer.

* * * * *